United States Patent [19]

Foglio et al.

[11] 4,077,970
[45] Mar. 7, 1978

[54] METHYL-a[3' ACETOXY-1'ISOPROPENYL]-3 SUBSTITUTED 1a,5a-4-THIA 2,6 DIAZA[3,2,0]2-HEPTENE-6 ACETATE 7-ONE

[75] Inventors: Maurizio Foglio; Antonino Suarato; Paolo Masi; Giovanni Franceschi; Giorgio Palamidessi; Luigi Bernardi, all of Milan, Italy

[73] Assignee: Societa' Farmaceutici Italia S.p.A., Milan, Italy

[21] Appl. No.: 603,605

[22] Filed: Aug. 11, 1975

[30] Foreign Application Priority Data

Aug. 15, 1974 United Kingdom ............... 35903/74

[51] Int. Cl.² .......................................... C07D 513/08
[52] U.S. Cl. ............................................. 260/306.7 C
[58] Field of Search ................................ 260/306.7 C

[56] References Cited

U.S. PATENT DOCUMENTS

| 3,862,164 | 1/1975 | Cooper | 260/306.7 C |
| 3,880,872 | 4/1975 | Kukolja et al. | 260/306.7 C |
| 3,900,487 | 8/1975 | Underwood et al. | 260/306.7 C |
| 3,927,013 | 12/1975 | Barton et al. | 260/306.7 C |

Primary Examiner—Donald G. Daus
Assistant Examiner—David E. Wheeler
Attorney, Agent, or Firm—Stevens, Davis, Miller & Mosher

[57] ABSTRACT

A process is disclosed for the preparation of a compound of the formula

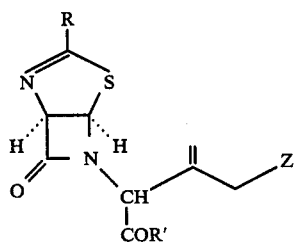

I where R and R¹ are defined herein below, wherein a compound of the structure;

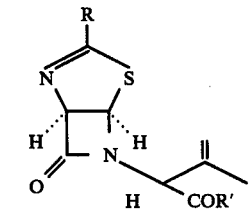

II is reacted in a suitable solvent with a haloamide in the presence of a metal oxide or a haloamide in the presence of a free radical initiator under the influence of light or heat or alternatively with a halogen in the presence of a metal oxide, to give a compound of the structure;

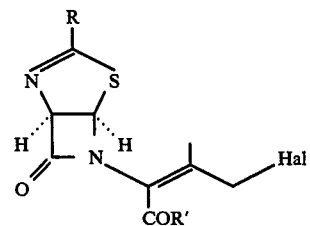

III which compound, in a suitable solvent is reacted with a suitable nucleophilic reagent to obtain the compound;

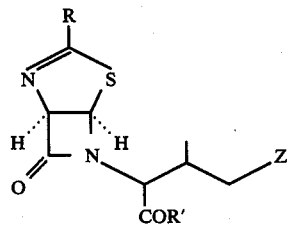

IV which compound is then subjected to allylic halogenation to give a compound of the structure;

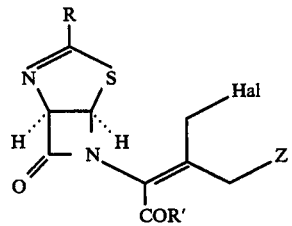

V which is then reacted with a reducing agent to yield I.

2 Claims, No Drawings

METHYL-α[3'ACETOXY-1'ISOPROPENYL]-3 SUBSTITUTED 1α,5X-4-THIA 2,6 DIAZA[3,2,0]2-HEPTENE-6 ACETATE 7-ONE

DISCLOSURE OF THE INVENTION

A new process is disclosed for the preparation of compounds of structure:

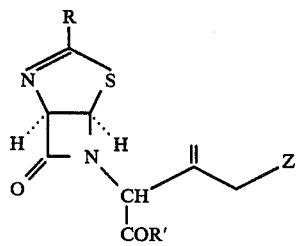

wherein R is a member selected from the class consisting of hydrogen, alkyl with not more than 12 carbon atoms, cycloalkyl with not more than 12 carbon atoms, alkenyl with not more than 12 carbon atoms, with or without substituents such as a free or a protected hydroxy group, amino, cyano and nitro groups, a thienyl-methyl, furyl-methyl, naphthyl-methyl, cyclohexenyl-methyl, and cyclohexadienyl-methyl, or one of the following groups:

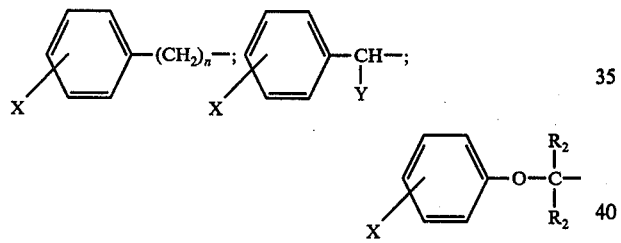

in which X is a member selected from the class consisting of hydrogen, halogen, a free or a protected hydroxy group, alkyl with 1 to 4 carbon atoms, nitro, cyano, and a protected amino group;

Y is a protected hydroxy, amino or carboxyl group;

n is an integer from 0 to 4;

$R^1$ is a member selected from the class consisting of hydroxy, alkoxy having from 1 to 4 carbon atoms, benzyloxy, p-methoxybenzyloxy, p-nitrobenzyloxy, benzhydryloxy, triphenyl methoxy, phenacyloxy, p-halophenacyloxy, phthalimidomethoxy, an amino group free or substituted by an alkyl having from 1 to 4 carbon atoms, cycloalkyl with 5 to 8 carbon atoms, phenyl, mononuclear heterocycle, acyloxymethyloxy, acylamidomethyloxy, free or protected hydrazino groups;

Z is a member selected from the class consisting of hydroxy, —O—Alkyl, —O—CO—Alkyl, O—CO—NH$_2$, —N$_3$, —NH$_2$, —S—Alkyl where the Alkyl is an alkyl group with 1 to 4 carbon atoms, —S—Aryl and —S—mononuclear heterocycle containing one or more nitrogen or sulfur atoms; and each $R^2$ is hydrogen or an alkyl group with 1 to 4 carbon atoms and the $R^2$'s may be the same or different characterized in that a compound of structure

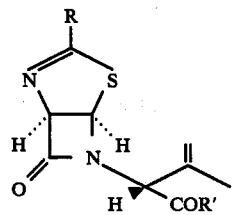

where R and $R^1$ have the meanings given above, is reacted in a suitable solvent with a haloamide in the presence of a metal oxide or a haloamide in the presence of a free radical initiator under the influence of light or heat or alternatively with a halogen in the presence of a metal oxide, to give a compound of structure:

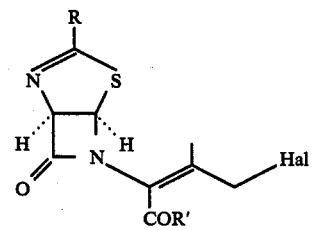

where R and $R^1$ have the meanings given above, Hal is a halogen atom;

the intermediate compound (III) in a suitable solvent is then reacted with an appropriate nucleophilic reagent to obtain the compound:

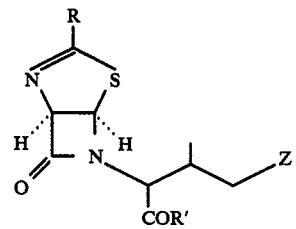

where R, $R^1$ and Z have the above meanings;

the compound (IV) is then subjected to an allylic halogenation in a suitable solvent by reacting it with a haloamide either under the influence of light alone or by heating it in the presence of a free radical initiator, to give a compound of structure:

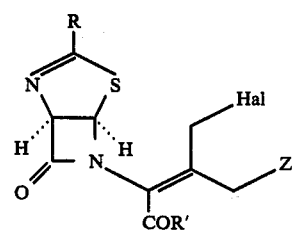

wherein R, $R^1$ and Hal and Z have the above meanings;

the intermediate compound (V) is then reacted with a reducing agent to give finally the desired compound (I).

This invention relates to a new process for the preparation of cephalosporins of structure (I), which are useful intermediates for the synthesis of derivatives of 7-amino-cephalosporanic acid (7-ACA) and of 7-amino-deacetoxycephalosporanic acid (7-ADCA) according to Foglio et al Italian application No. 23,070 A/74, Case G.331, corresponding to allowed U.S. application Ser. 662,338 which is a C.I.P. of Ser. No. 578,875 filed May 19, 1975, now abandoned and Foglio British application No. 34,724/74, Case G.338, corresponding to U.S. application Ser. No. 601,586 filed Aug. 4, 1975, now U.S. Pat. No. 4,018,776.

The process of the present invention is illustrated by the following reaction scheme:

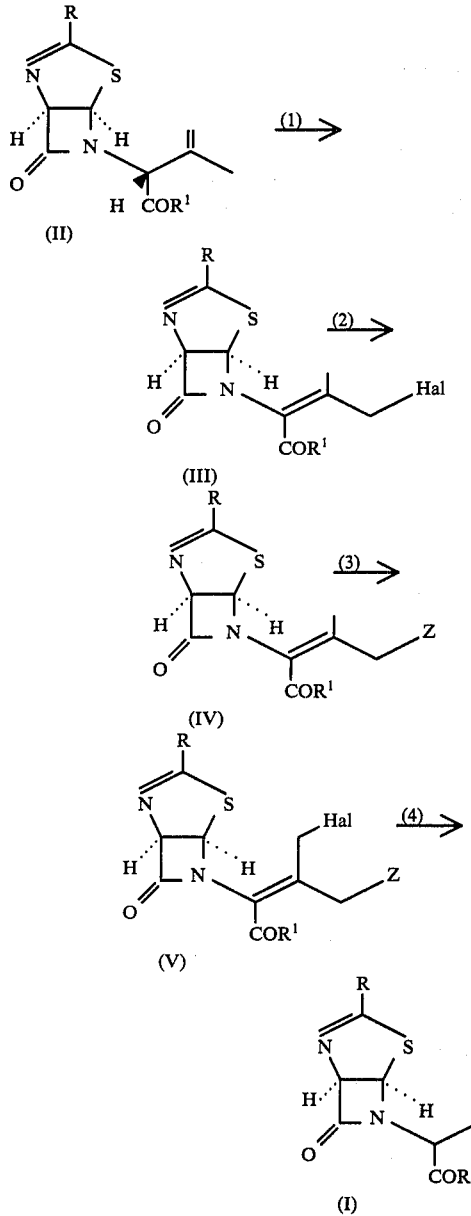

wherein R is a member selected from the class consisting of hydrogen, alkyl, cycloalkyl, alkenyl with not more than 12 carbon atoms, with or without substituents such as free or protected hydroxy group, amino, cyano and nitro groups, thienyl-methyl, furyl-methyl, naphthyl-methyl, cyclohexenyl-methyl, and cyclohexadienyl-methyl, or one of the following groups:

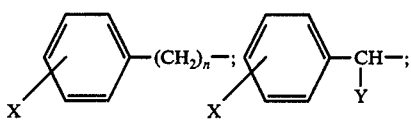

-continued

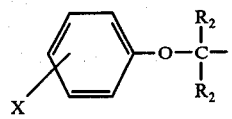

in which X is a member selected from the class consisting of hydrogen, halogen, a free or protected hydroxy group, alkyl with 1 to 4 carbon atoms, nitro, cyano and a protected amino group;

Y is a protected hydroxy, amino or carboxyl group;

n is an integer from 0 to 4;

$R^1$ is a member selected from the class consisting of hydroxy, alkoxy having from 1 to 4 carbon atoms, benzyloxy, p-methoxybenzyloxy, p-nitrobenzyloxy, benzhydryloxy, triphenyl methoxy, phenacyloxy, p-halophenacyloxy, phthalimido-methoxy, an amino group free or substituted by an alkyl having from 1 to 4 carbon atoms, cycloalkyl with 5 to 8 carbon atoms, phenyl, a mononuclear heterocycle, acyloxymethyloxy, acylamidomethyloxy, free or protected hydrazino groups;

Hal is an halogen atom, preferably chlorine or bromine;

Z is a member selected from the class consisting of hydroxy, O—Alkyl, O—CO—Alkyl, —OCONH$_2$, —N$_3$, —NH$_2$, —S—Alkyl where Alkyl is an alkyl group with 1 to 4 carbon atoms, —S—aryl and —S—mononuclear heterocycle containing one or more nitrogen or sulfur atoms; and each $R^2$ is hydrogen or an alkyl group with 1 to 4 carbon atoms and the $R^2$'s may be the same or different.

Step (1) can be accomplished by reacting the starting compound (II) in a suitable solvent either (a) with a haloamide, such as N-chloro-, N-bromo- or N-iodo-succinimide in the presence of metal oxides, such as Al$_2$O$_3$, or alternatively (b) with a haloamide under the influence of light alone, or in the presence of free radical initiators such as azo-bis-isobutyronitrile and similar compounds under the influence of light or heat.

Moreover, step (1) can be accomplished by reacting the starting compound (II) in a suitable solvent with a halogen, preferably chlorine or bromine, in the presence of a metal oxide, such as CaO, HgO, Ag$_2$O and the like.

Step (2) is a nucleophilic substitution reaction and can be accomplished by reacting compound (III) in a suitable solvent with appropriate nucleophic reactants having the same residue as those indicated by the substituent Z.

Step (3) is an allylic halogenation and it can be accomplished by reacting compound (IV) in a suitable solvent with a haloamide either (a) under the influence of light alone or (b) with heating in the presence of free radical initiators such as azo-bis-isobutyronitrile and similar compounds.

In step (4) the halogen is reductively split off with simultaneous shifting of the double bond and formation of the desired compound (I). This reaction is carried out by using reducing agents per se well known in the art, such as zinc dust in protic solvents, chromium -(II)-salts and the like, or by means of electrolytical methods.

Compounds (I) obtained according to this novel synthesis can be easily transformed into the corresponding cephalosporin derivatives as described in the co-pending patent applications mentioned above.

The following non-limiting examples serve to illustrate the invention still further:

EXAMPLE 1

Methyl-α-bromoisopropylidene-3-phenoxymethyl-1α,-5α-4-thia-2,6-diaza[3.2.0]-2-heptene-6-acetate-7-one (VII).

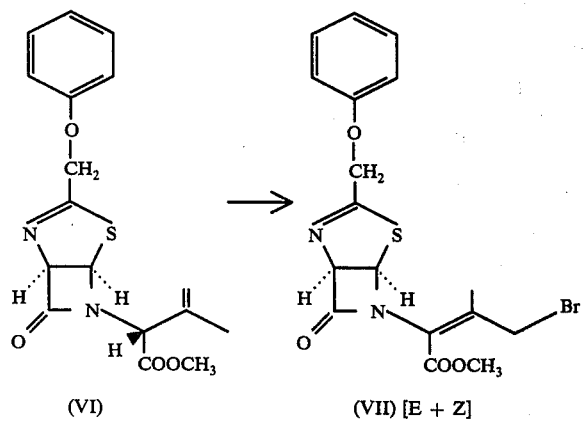

(VI)                    (VII) [E + Z]

To a solution of methyl-α-isopropenyl-3-phenoxymethyl-1α,5α-4-thia-2,6-diaza[3.2.0]-2-heptene-6-acetate-7-one, (VI), (8 g), in benzene (200 ml), N-bromo-succinimide (7 g) and Al$_2$O$_3$ (40 g) are added and the resulting suspension is stirred for 20 h. After filtration, the solvent is removed in vacuo and the residue is chromagraphed (silica gel; benzene/ethyl acetate 95:5) to give 8.2 g of (VII) as a mixture of two stereoisomers (E + Z).

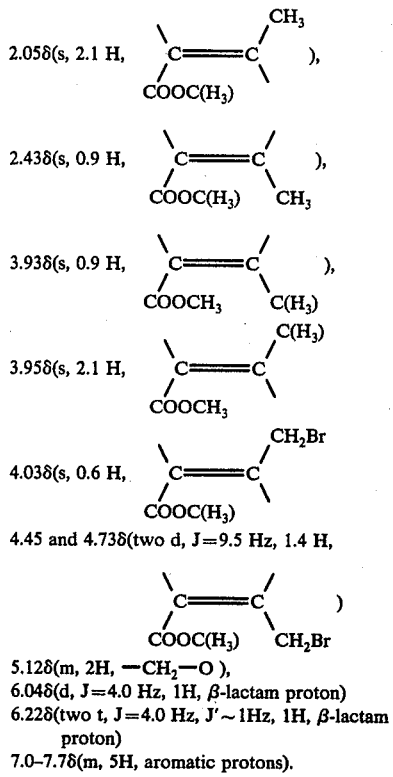

PMR(CDCl$_3$):
2.05δ(s, 2.1 H, [structure]),
2.43δ(s, 0.9 H, [structure]),
3.93δ(s, 0.9 H, [structure]),
3.95δ(s, 2.1 H, [structure]),
4.03δ(s, 0.6 H, [structure]),
4.45 and 4.73δ(two d, J=9.5 Hz, 1.4 H, [structure])
5.12δ(m, 2H, —CH$_2$—O ),
6.04δ(d, J=4.0 Hz, 1H, β-lactam proton)
6.22δ(two t, J=4.0 Hz, J'~1Hz, 1H, β-lactam proton)
7.0–7.7δ(m, 5H, aromatic protons).

EXAMPLE 2

Methyl-α-bromoisopropylidene-3-phenoxymethyl-1α,-5α-4-thia-2,6-diaza[3.2.0]-2-heptene-6-acetate-7-one (VII).

Compound (VI), (3.46 g), is dissolved in CCl$_4$ (200 ml). CaO (4 g) is added and to the resulting stirred suspension, a solution of bromine (1.92 g) in CCl$_4$ (10 ml) is added dropwise at room temperature. After 20 minutes, the insoluble material is filtered off and the solvent evaporated in vacuo. The residue is chromatographed (silica gel; benzene/ethyl acetate 95/5) to give 3.3 g of compound (VII) as a mixture of two stereoisomers (E + Z).

EXAMPLE 3

Methyl-α-bromoisopropylidene-3-phenyl-1α,5α-4-thia-2,6-diaza-[3.2.0]-2-heptene-6-acetate-7-one (IX).

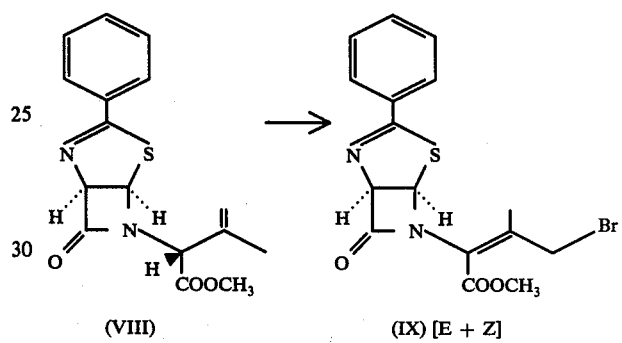

(VIII)                   (IX) [E + Z]

To a solution of methyl-α-isopropenyl-3-phenyl-1α,5α-4-thia-2,6-diaza[3.2.9]-2-heptene-6-acetate-7-one, (VIII), (8 g), in benzene (200 ml), N-bromosuccinimide (7g) and Al$_2$O$_3$ (40 g) are added and the resulting suspension is stirred for 20 hours. After filtration, the solvent is removed in vacuo and the residue is taken up in CCl$_4$ and filtered. Evaporation of the solvent gives 9 g of compound (IX) as a mixture of stereoisomers (E + Z).

PMR (CDCl$_3$):
1.98δ(s, 1.8 H, [structure]),
2.31δ(s, 1.2 H, [structure]),
3.76δ(s, 1.2 H, [structure]),
3.82δ (s, 1.8 H, [structure]),

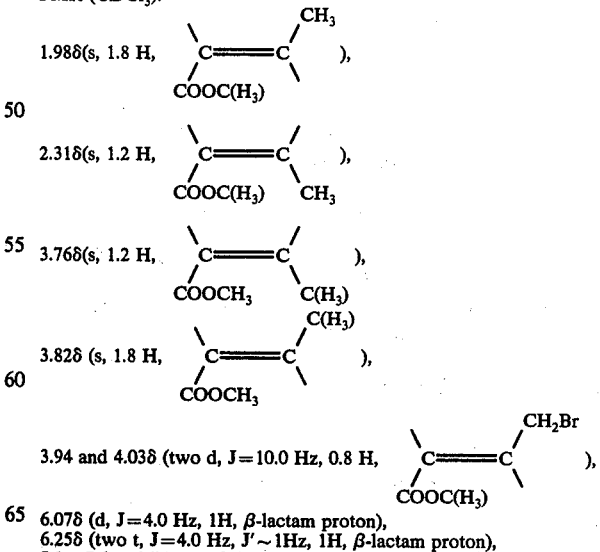

3.94 and 4.03δ (two d, J=10.0 Hz, 0.8 H, [structure]),
6.07δ (d, J=4.0 Hz, 1H, β-lactam proton),
6.25δ (two t, J=4.0 Hz, J'~1Hz, 1H, β-lactam proton),
7.2 – 7.6 and 7.7 – 8.0δ (m, 5H, aromatic protons).

EXAMPLE 4

Methyl-α-acetoxyisopropylidene-3-phenoxymethyl-1α,5α-4-thia-2,6-diaza[3.2.0]-2-heptene-6-acetate-7-one (X).

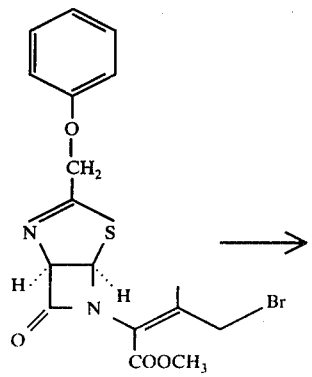
(VII) [E+Z]

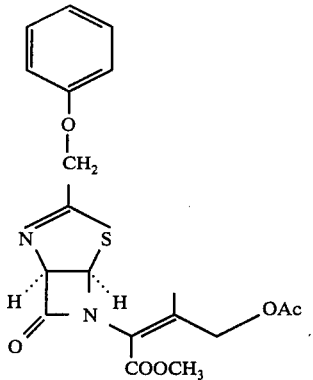
(X) [E+Z]

To a solution of compound (VII), (7g), in dry acetone (70 ml), potassium acetate (10 g) is added and the resulting suspension is stirred 24 hours at room temperature. After filtering off the insoluble material, the solvent is evaporated in vacuo to give a residue (6.2 g) consisting of two stereoisomers which can be separated by column chromatography (silica gel; benzene/ethyl acetate 98/2). The spectroscopic data of the E and Z components are reported.

E-isomer-m.p. 76°–77° C (ethyl ether):
PMR (CDCl₃): 1.75

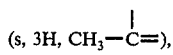
(s, 3H, CH₃—C=), 2.05 (s, 3H, CH₃—CO—), 3.78 (s, 3H, CH₃O—), 4.99 (d, J 1Hz), 2H, CH₂—O—C₆H₅), 5.13 (s, 2H, CH₂—O—CO—C (H₃)), 5.88 (d, J=4.0 Hz, 1H, β-lactam proton), 6.07 (two t, J=4.0 Hz and J 1Hz, 1H, β-lactam proton) and 6.85 - 7.55 (m, 5H, aromatic protons).

Z-isomer:
PMR (CDCl₃): 2.04 and 2.21 (two s, 3H each,

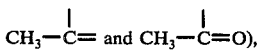
CH₃—C= and CH₃—C=O), 3.81 (s, 3H, CH₃O), 4.63 (s, 2H, CH₂—O), 5.02 (dd, 2H, CH₂—O—CO), 5.90 and 6.10 (dd, J=4Hz, 2H, H of β-lactam), 6.8 - 7.5 (m, 5H, C₆H₅).

EXAMPLE 5

Methyl-α-acetoxyisopropylidene-3-phenyl-1α,5α-4-thia-2, 6-diaza-[3.2.0]-2-heptene-6-acetate-7-one (XI).

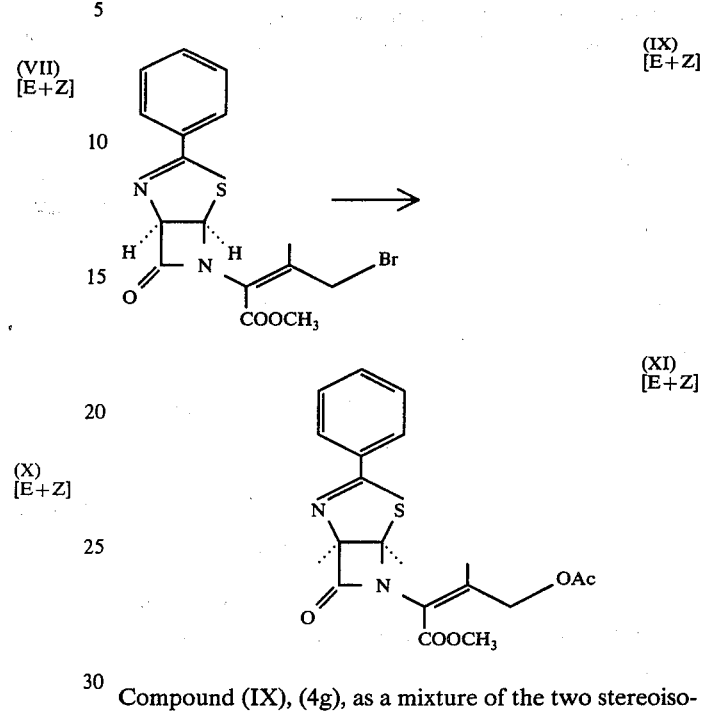

Compound (IX), (4g), as a mixture of the two stereoisomers, is dissolved in dry acetone (80 ml), treated with potassium acetate (8 g) and the suspension stirred for 24 hours at room temperature. The salts are filtered off and the solvent evaporated in vacuo to give compound (XI) (3.7 g) as a mixture of the stereoisomers.

PMR(CDCl₃): 1.87δ(s, 2.2 H, \[CH₃ / C=C / COOC(H₃)\]), 1.99δ(s, 0.8 H, \[C(H₂)—O—CO—CH₃ / C=C / COOC(H₃)\]), 2.08δ(s, 2.2 H, \[C=C / C(H₂)—O—CO—CH₃ / COOC(H₃)\]), 2.20δ(s, 0.8 H, \[C=C / COOC(H₃) CH₃\]), 3.82δ(s, 3H, OCH₃), 4.69δ(s, 0.5 H, \[CH₂— / C=C / COOC(H₃)\]), 5.20δ(s, 1.5 H, \[C=C / CH₂— / COOC(H₃)\]), 6.08 and 6.27δ(two d, J = 4.0 Hz. 2 H, β-lactam protons), 7.3 – 7.6 and 7.7 –

8.0δ(m, 5H, aromatic protons).

EXAMPLE 6

Methyl-α-phenylthioisopropylidene-3-phenoxymethyl-1α,5α-4-thia-2,6-diaza[3.2.0]-2-heptene-6-acetate-7-one (XII).

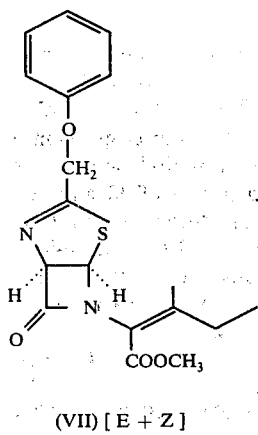

(VII) [ E + Z ]

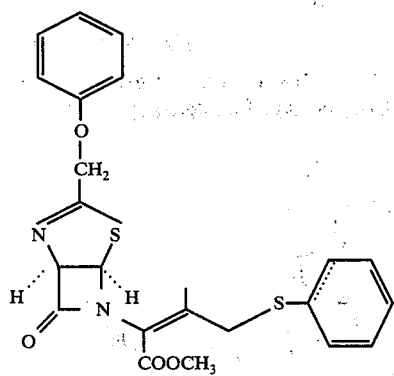

(XII) [ E + Z ]

Compound (VII), (0.3 g) as a mixture of the two stereoisomers, is dissolved in dry acetone (20 ml), treated with potassium thiophenate (0.3 g) and left under stirring for 30 minutes at 35° C. The salts are filtered off and the solvent is evaporated in vacuo to give compound (XII), (0.310 g), as a mixture of the two stereoisomers which can be separated by column chromatography (silica gel; benzene/ethyl acetate 95/5).

The NMR of the main component is here reported:
PMR (CDCl$_3$): 1.90δ (s, 3H, CH$_3$), 3.53δ (s, 3H, CH$_3$O), 4.53 and 4.75δ (two d, J=13.5Hz, 2H, CH$_2$-S), 4.98δ (d, J~1 Hz, 2H, CH$_2$—O), 5.80δ (d, j=4Hz, 1H, β-lactam proton), 6.05δ (two t, J=4Hz, J~1 Hz, 1H, β-lactam proton), 6.8 - 8.1δ (m, 10 H, aromatic protons).

EXAMPLE 7

Methyl-α-[1'-bromo-3'-acetoxyisopropylidene]-3-phenyl-1α-5=-4-thia-2,6-diaza[3.2.0]-2-heptene-6-acetate-7-one (XIII).

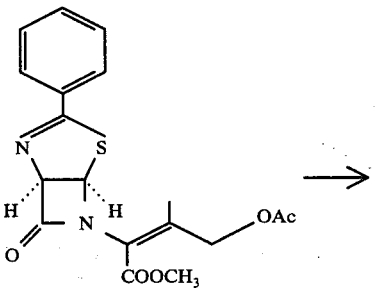

(XI) [E + Z]

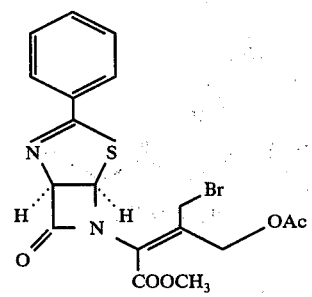

(XIII) [E + Z]

Compound (XI), (0.2 g), as a mixture of the two stereoisomers, is dissolved in benzene (30 ml), treated with N-bromosuccinimide (1 g) and the resulting solution irradiated with a tungsten lamp (500 W) for 30 minutes at room temperature. After evaporation of the solvent in vacuo the residue is chromatographed (silica gel; benzene/chloroform) to give compound (XIII), (0.15 g), as a mixture of the E and Z isomers.

E-isomer:
PMR(CDCl$_3$): 2.01δ (s, 3H, CH$_3$—CO), 3.87δ (s, 3H, CH$_3$O), 4.53δ (s, 2H, CH$_2$Br), 4.83δ (s, 2H, CH$_2$—O—CO—), 6.07 and 6.26δ (two d, J=4.0 Hz, 2H, β-lactam protons), 7.3 - 8.1δ (m, 5H, aromatic protons).

Z-isomer:
PMR(CDCl$_3$): 2.10 (s, 3H, CH$_3$—CO), 3.85 (s, 3H, CH$_3$O), 4.13 (S, 2H, CH$_2$Br), 5.22 (dd, 2H, CH$_2$—O—CO), 6.08 and 6.31 (dd, J 4.3 Hz, 2H, H of β-lactam), 7.6 - 8.3 (m, 5H, C$_6$H$_5$).

EXAMPLE 8

Methyl-α-[3'-acetoxy-1'-isopropenyl]-3-phenyl-1α,5α-4-thia-2,6-diaza[3.2.0]-2-heptene-6-acetate-7-one (XIV).

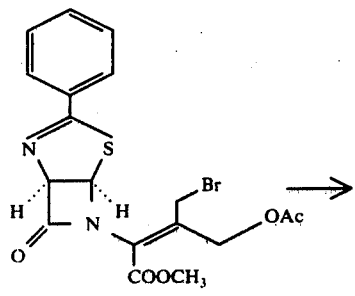

(XIII)

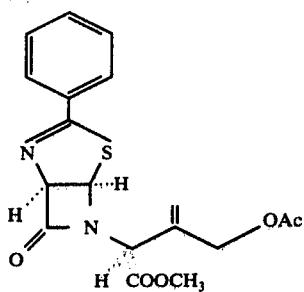

(XIV)

Compound (XIII), (1 g), is dissolved in cold 90% acetic acid (20 ml) and treated with an excess of zinc metal dust. After stirring 30 minutes, water (100 ml) and ethyl acetate (100 ml) are added and the organic layer is separated, filtered, and washed with water. The solvent is then evaporated and the residue chromatographed (silica gel; benzene/ethyl acetate 95/5) to give compound (XIV), (0.450 g), as mixture of two epimers.

PMR (CDCl$_3$): 2.02 and 2.08 (two s, 3H, CH$_3$—CO), 3.77 and 3.80 (two s, 3H, CH$_3$O), 4.68 (s, 1.7 H, CH$_2$—O—CO), 4.9 – 5.7 (m, 3.3 H, CH —CH$_2$—O—CO and =CH$_2$), 5.8 – 6.3 (m, 2H, H of β-lactam), 7.4 – 8.1 (m, 5H, C$_6$H$_5$).

EXAMPLE 9

Methyl-α-bromoisopropylidene-3-tert-butyl-1α,5α-4-thia-2,5-diaza-[3.2.0]-2-heptene-6-acetate-7-one (XVI).

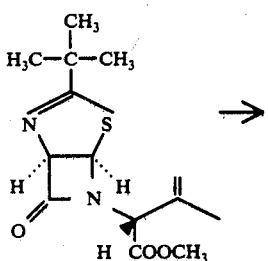

(XV)

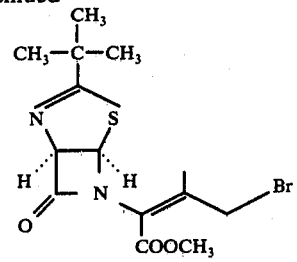

(XVI) [E + Z isomers]]

3.0 g of CaO dust is suspended in a solution of 2.96 of methyl-α-isopropenyl-3-tert-butyl-1α,5α-4-thia-2,6-diaza[3.2.0]-2-heptene-6-acetate-7-one (XV) in 100 ml of methylene chloride, and to the resulting suspension a solution of 1 ml of bromine in 50 of methylene chloride is added under stirring within a period of 30 minutes. After elimination of the insoluble material by filstration, the solvent is removed in vacuo and the crude residue (3.8 g) is chromatographed on a silica-gel column eluted with benzene-ethyl acetate (98:2 v.v.) to give (XVI) (3.2 g) as a mixture of E and Z isomers.

PMR(CDCl$_3$) of the E isomer: 1.30δ (s, 9H, (CH$_3$)$_3$C—), 2.02δ (s, 3H, CH$_3$—C=), 3.87δ (s, 3H, COOCH$_3$), 4.35 and 4.70δ (two d, 2H, J=9.5Hz, —CH$_2$—Br), 5.92 and 6.05δ (two d, J=4Hz, 2H, β-lactam protons).

EXAMPLE 10

Methyl-α-acetoxyisopropylidene-3-tert-butyl-1α,5α-4-thia-2,6-diaza-[3.2.0]-2-heptene-6-acetate-7-one (XVII).

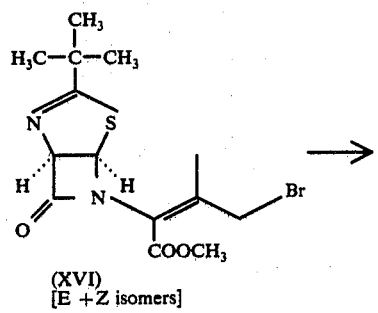

(XVI) [E +Z isomers]

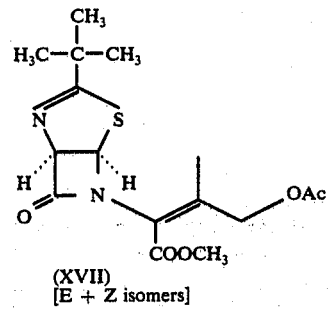

(XVII) [E + Z isomers]

3.0 g of methyl-α-bromoisopropylidene-3-tert-butyl-1α,5α-4-thia-2,6-diaza[3.2.0]-2-heptene-6-acetate-7-one (XVI), as a mixture of E and Z isomers, are dissolved in 50 ml of acetone, treated with 3.0 g of anhydrous potassium acetate and stirred overnight at 40° C. After cooling, the insoluble material is removed by filtration and the solvent evaporated in vacuo to give crude (XVII) as a mixture of E and Z isomers. The isomers are separated by fractional crystallization from diethyl ether-petroleum ether.

PMR(CDCl$_3$) of the E isomer: 1.92δ (s, 9H, (CH$_3$)$_3$—C—), 1.90δ (s, 3H, CH$_3$—C=), 2.12δ (s, 3H, CH$_3$CO), 3.84δ (s, 3H, CH$_3$O—), 5.21δ (s, 2H, CH$_2$OCO—), 5.88δ and 6.05δ (two d, 2H, β-lactam protons).

EXAMPLE 11

Benzhydryl-α-bromoisopropylidene-3-phenoxymethyl-1α,5α-4-thia-2,6-diaza[3.2.0]-2-heptene-6-acetate-7-one (XIX).

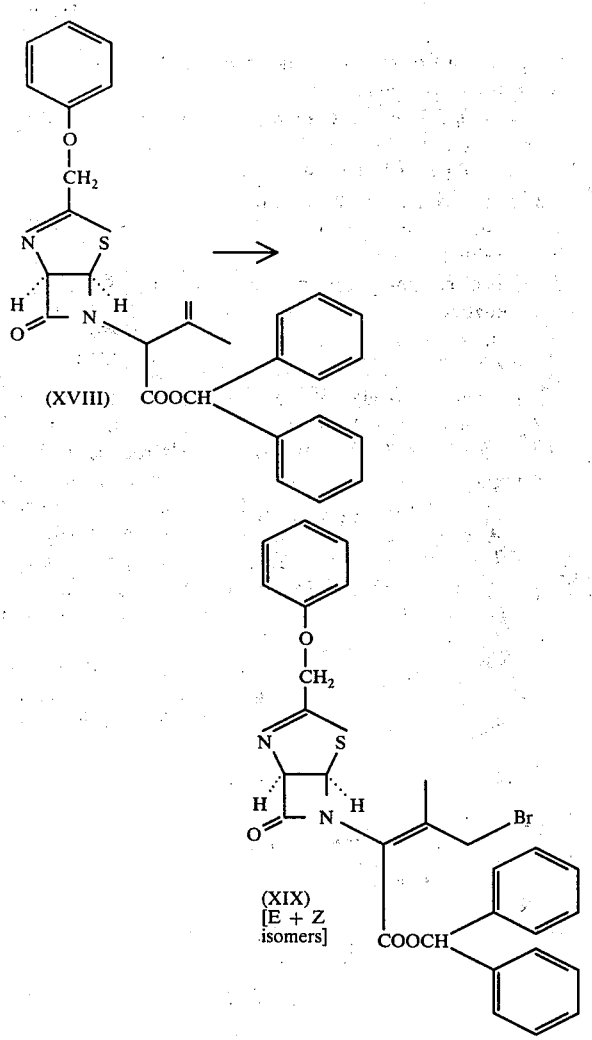

5.0 g of benzhydryl-α-isopropenyl-3-phenoxymethyl-1α,5α-4-thia-2,6-diaza[3.2.0]-2-heptene-6-acetate-7-one (XVIII) are dissolved in methylene chloride and treated with 5.0 g of barium oxide. To the resulting suspension, 1 ml of bromine in 50 ml of methylene chloride is added dropwise under stirring at room temperature. The insoluble material is then filtered off, the solvent removed in vacuo, and the residue chromatographed on a silica gel column eluted with benzene/ethyl acetate to yield (XIX) (5.2 g) as a mixture of E and Z isomers. PMR(CDCl$_3$) of the E isomer: 1.92δ (s, CH$_3$C=), 4.24 and 4.75δ (two d, CH$_2$—Br), 5.78 and 6.05δ (two d, 2H, β-lactam protons), 6.7 – 7.5δ (m, 16H, aromatic protons and CH—OCO—).

PMR(CDCl$_3$) of the Z isomer: 2.31δ (s, CH$_3$C=), 3.90δ (s, CH$_2$Br), 5.78 and 6.05δ (two d, 2H, β-lactam protons), 6.7 and 7.5δ (m, 16H, aromatic protons and CH—OCO).

EXAMPLE 12

Benzhydryl-α-acetoxyisopropylidene-3-phenoxymethyl-1α,5α-4-thia-2,6-diaza[3.2.0]-2-heptene-6-acetate-7-one (XX).

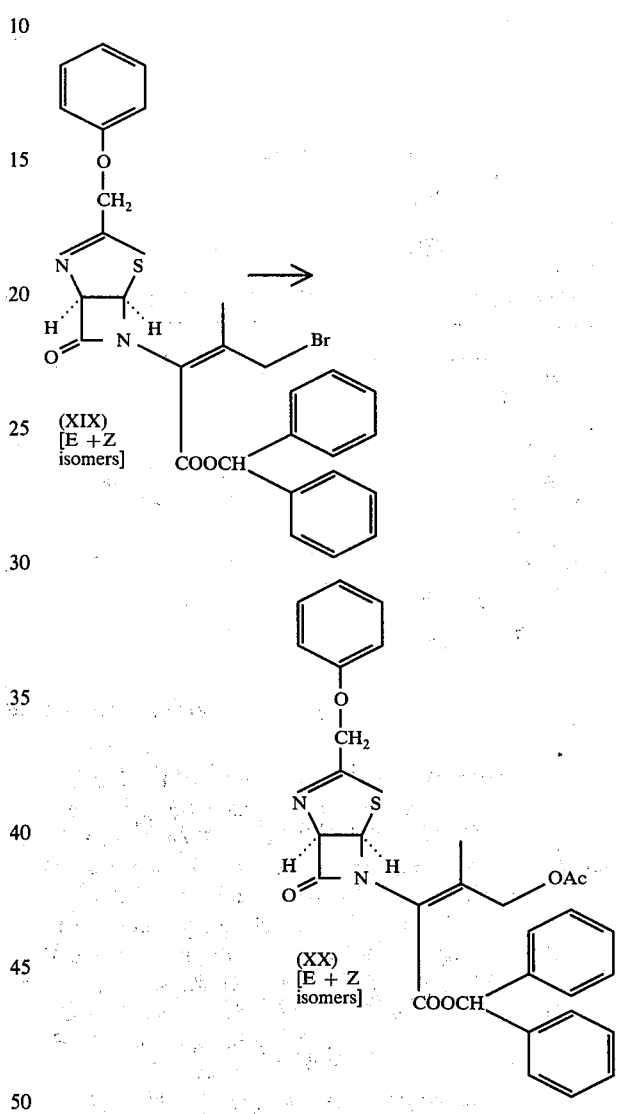

5.0 g of benzhydryl-α-bromoisopropylidene-3-phenoxymethyl-1α,5α-4-thia-2,6-diaza[3.2.0-2-heptene-6-acetate-7-one (XIX), as a mixture of E and Z isomers, are dissolved in 50 ml of acetonitrile, treated with 5.0 g of anhydrous potassium acetate and stirred overnight at 40° C. After cooling, the insoluble material is removed by filtration and the solvent evaporated in vacuo to give crude (XX) as a mixture of E and Z isomers. The isomers are separated by chromatography on a silica gel column eluted with benzene-ethyl acetate.

PMR(CDCl$_3$) of the E isomer: 1.83δ (s, 3H, CH$_3$C=), 2.05δ (s, 3H, CH$_3$CO), 4.85δ (broad s, 2H, CH$_2$—OC$_6$(H$_5$)), 5.15δ (s, 2H, CH$_2$OCO), 5.76 and 6.06δ (two d, 2H, β-lactam protons), 6.9 – 7.7δ (m, 16H, aromatic protons and CHOCO).

EXAMPLE 13

Methyl-α-(1'-bromo-3'-acetoxyisopropylidene)-3-methyl-1α,5α-4-thia-2,6-diaze[3.2.0]-2-heptene-6-acetate-7-one (XXII).

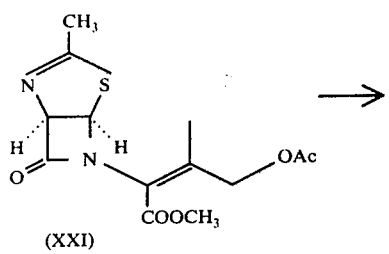

(XXI)

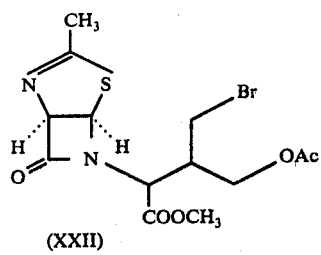

(XXII)

A solution of 0.650 g of methyl-α-acetoxyisopropylidene-3-methyl-1α,5α-4-thia-2,6-diaza[3.2.0]-3-heptene-6-acetate-7-one, (XXI), (E isomer) in 40 ml of benzene is treated with 1.0 g of N-bromosuccinimide and refluxed for 10 minutes in a nitrogen atmosphere under irradiation by a 500 W tungsten lamp. After elimination of succinimide, the crude product, only partially brominated, is again treated with 0.650 g of N-bromo-succinimide under the same conditions as just described. The reaction mixture, after evaporation of the solvent, is chromatographed on a silica-gel column eluted with benzene-ethyl acetate to give compound (XXII) (250 mg).

EXAMPLE 14

Methyl-α-[3'-acetoxy-1'-isopropenyl]-3-methyl-1α,5α-4-thia-2,6-diaza[3.2.0]-2-heptene-6-acetate-7-one (XXIII).

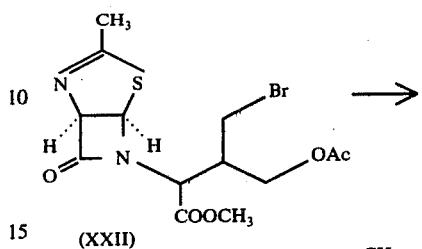

(XXII)

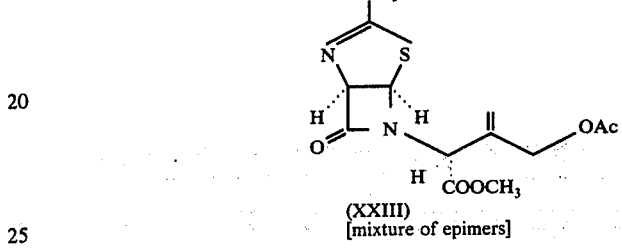

(XXIII)
[mixture of epimers]

A solution of 0.50 g of methyl-α-[1'-bromo-3'-acetoxyisopropylidene]-3-methyl-1α,5α-4-thia-2,6-diaza[3.2.0]-2-heptene-6-acetate-7-one (XXII) (Z isomer), in 5 ml of tetrahydrofuran, is cooled to 0° C and treated with 20 ml of 20% aq. acetic acid and 0.500 g of zinc dust. After stirring for 30 minutes, the insoluble material is filtered off and the filtrate neutralized with a saturated solution of $NaHCO_3$. Extraction with ethyl acetate gives 300 mg of (XXIII) as a mixture of two epimers which can be separated by column chromatography (silica-gel eluted with benzene-ethyl acetate 85-15 v.v.)

PMR($CDCl_3$) of the main component: 2.10δ (s, 3H, $CH_3CO$), 2.30δ (d, J~1$H_z$, 3H, $CH_3$—C=), 3.79δ (s, 3H, $CH_3O$—), 4.65δ (s, 2H, $CH_2$—OCO), 4.95δ (s, 1H,

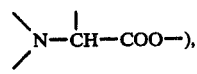

5.37δ and 5.52δ (two m, 1H each, =$CH_2$), 5.77δ (d, J=4.5$H_z$, 1H, > N-CH-S), 5.95δ (dq,J=4.5$H_z$ J'~1$H_z$, 1H,

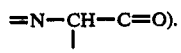

What is claimed is:
1. Methyl-α-[3'-acetoxy-1'-isopropenyl]-3-phenyl1α,-5α-4-thia-2,6-diaza-[3,2,0]-2-heptene-6-acetate-7-one.
2. Methyl-α-[3'-acetoxy-1'-isopropenyl]-3-methyl-1α,5α-4-thia-2,6-diaza[3,2,0]-2-heptene-6-acetate-7-one.

* * * * *